(12) United States Patent
Richter et al.

(10) Patent No.: US 11,903,620 B2
(45) Date of Patent: Feb. 20, 2024

(54) FLEXIBLE SLEEVE FOR BONE FIXATION, AND RELATED SYSTEMS AND METHODS

(71) Applicant: Medos International Sarl, Le Locle (CH)

(72) Inventors: Joern Richter, Kandern (DE); Rainer Ponzer, Himmelreid (CH)

(73) Assignee: Medos International Sarl (CH)

( * ) Notice: Subject to any disclaimer, the term of this patent is extended or adjusted under 35 U.S.C. 154(b) by 0 days.

(21) Appl. No.: 17/156,874

(22) Filed: Jan. 25, 2021

(65) Prior Publication Data

US 2022/0233218 A1    Jul. 28, 2022

(51) Int. Cl.
*A61B 17/70* (2006.01)
*A61B 17/86* (2006.01)

(52) U.S. Cl.
CPC ...... *A61B 17/7082* (2013.01); *A61B 17/7091* (2013.01); *A61B 17/866* (2013.01); *A61B 17/8685* (2013.01)

(58) Field of Classification Search
CPC ....... A61B 17/34–3498; A61B 17/7074–7092; A61B 17/7082; A61B 17/8875–8894
See application file for complete search history.

(56) References Cited

U.S. PATENT DOCUMENTS

| | | | | |
|---|---|---|---|---|
| 5,320,611 A * | 6/1994 | Bonutti | ............ | A61M 25/0084 604/530 |
| 7,927,360 B2 * | 4/2011 | Pond, Jr. | ............ | A61B 17/7037 606/267 |
| 8,211,156 B2 | 7/2012 | Andersen et al. | | |
| 8,262,662 B2 * | 9/2012 | Beardsley | ............ | A61B 17/708 606/86 A |
| 8,372,131 B2 | 2/2013 | Hestad et al. | | |
| 8,956,361 B2 * | 2/2015 | Davenport | ......... | A61B 17/7032 606/104 |
| 9,198,698 B1 * | 12/2015 | Doose | ................ | A61B 17/7085 |
| 9,408,716 B1 * | 8/2016 | Reitblat | ................ | A61B 17/70 |
| 10,058,355 B2 | 8/2018 | Beyer | | |
| 10,105,165 B2 | 10/2018 | Biedermann et al. | | |
| 10,136,923 B2 | 11/2018 | Keyer et al. | | |
| 10,188,442 B2 * | 1/2019 | Mazel | ............... | A61M 5/14276 |
| 10,285,740 B2 | 5/2019 | May et al. | | |
| 10,973,558 B2 * | 4/2021 | Kam | .................. | A61B 17/7082 |
| 11,234,830 B2 * | 2/2022 | Mesiwala | ............ | A61B 17/863 |

(Continued)

*Primary Examiner* — Eduardo C Robert
*Assistant Examiner* — Steven J Cotroneo
(74) *Attorney, Agent, or Firm* — BakerHostetler

(57) ABSTRACT

A flexible tubular member for guiding insertion of instrumentation to a bone screw affixed within bone includes a tubular body that is flexible, constructed of textile material, and defines a longitudinal axis. The tubular body also defines a proximal end and a distal end opposite each other along the longitudinal axis. The tubular body further defines a guide channel that extends from a proximal opening at the proximal end to a distal opening at the distal end. An attachment member is located at the distal end of the tubular body and is configured to couple the distal end to a proximal portion of the bone screw. The attachment member has an annular shape around the guide channel and is configured to expand responsive to a predetermined tensile force applied to the tubular body for decoupling from the bone screw.

8 Claims, 8 Drawing Sheets

(56) References Cited

U.S. PATENT DOCUMENTS

| | | |
|---|---|---|
| 2006/0079903 A1 | 4/2006 | Wong |
| 2006/0212062 A1* | 9/2006 | Farascioni ......... A61B 17/3439 606/191 |
| 2007/0032703 A1 | 2/2007 | Sankaran et al. |
| 2008/0114403 A1* | 5/2008 | Kuester ............. A61B 17/7037 606/264 |
| 2010/0049003 A1 | 2/2010 | Levy |
| 2010/0331883 A1* | 12/2010 | Schmitz ............ A61B 17/0218 606/279 |
| 2012/0071784 A1 | 3/2012 | Melkent et al. |
| 2013/0053851 A1 | 2/2013 | Schmitz et al. |
| 2013/0211538 A1* | 8/2013 | Hestad ............... A61B 17/3423 623/23.7 |
| 2018/0256146 A1 | 9/2018 | Chen et al. |
| 2019/0150989 A1* | 5/2019 | Biester ................ A61B 17/863 |
| 2020/0306055 A1* | 10/2020 | Greenhalgh ......... A61B 17/869 |
| 2021/0068980 A1* | 3/2021 | Wall ...................... A61B 34/10 |
| 2021/0153968 A1* | 5/2021 | Peterson ............ A61B 17/7082 |

\* cited by examiner

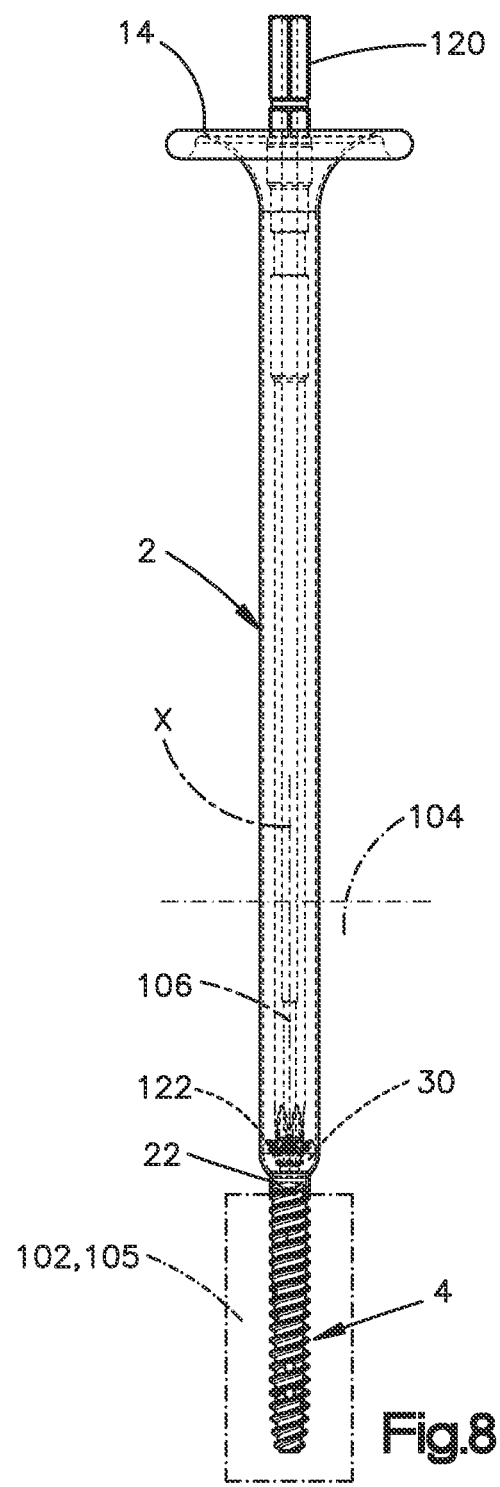
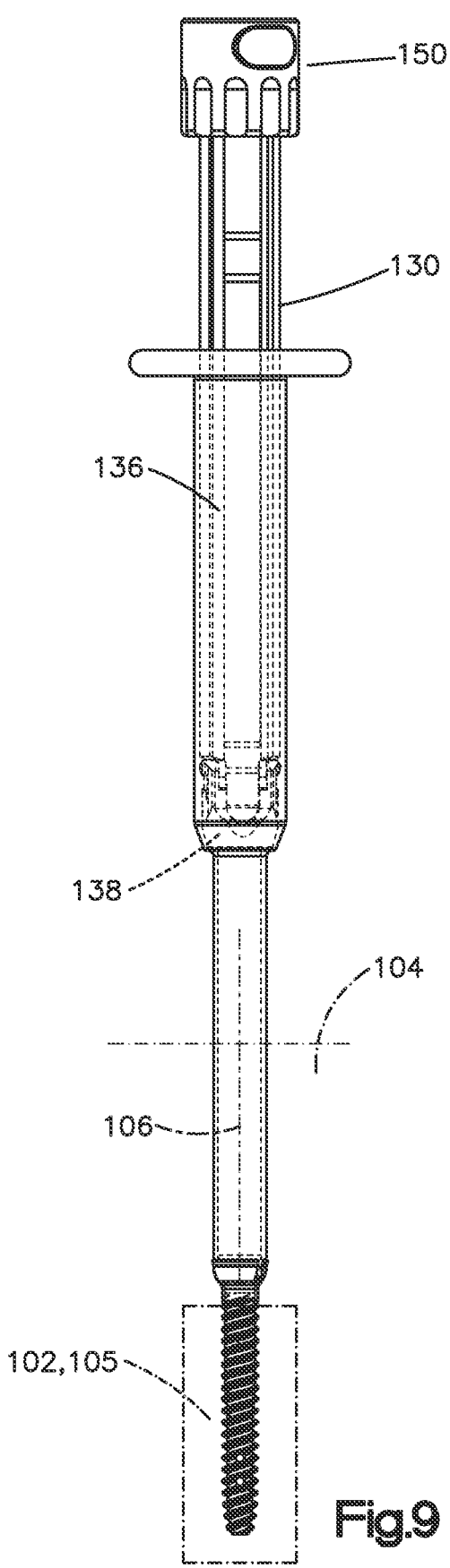

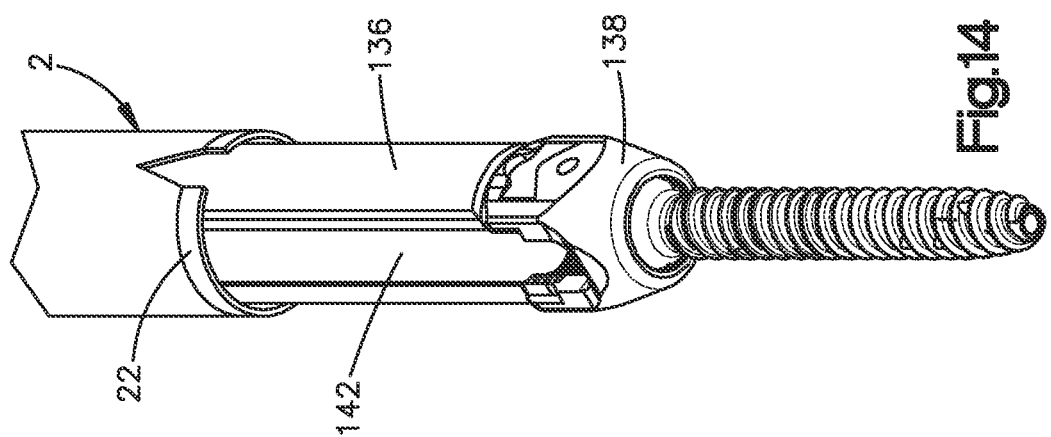
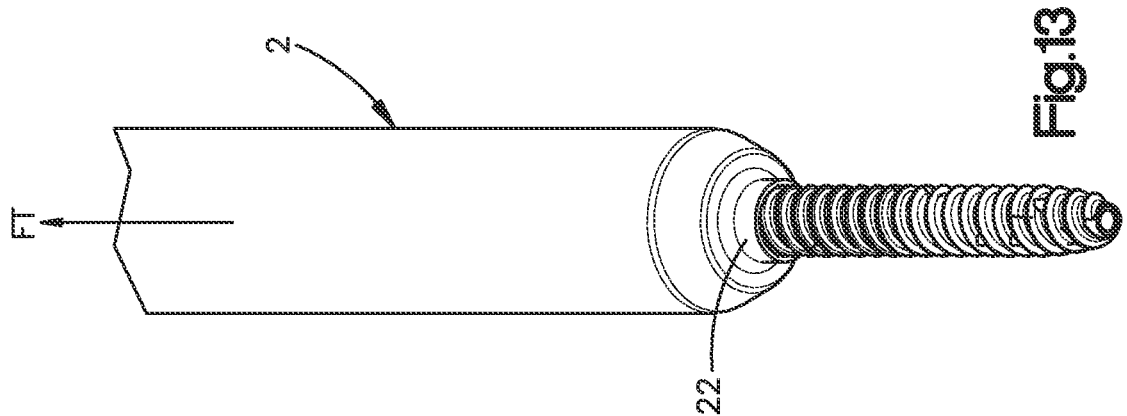
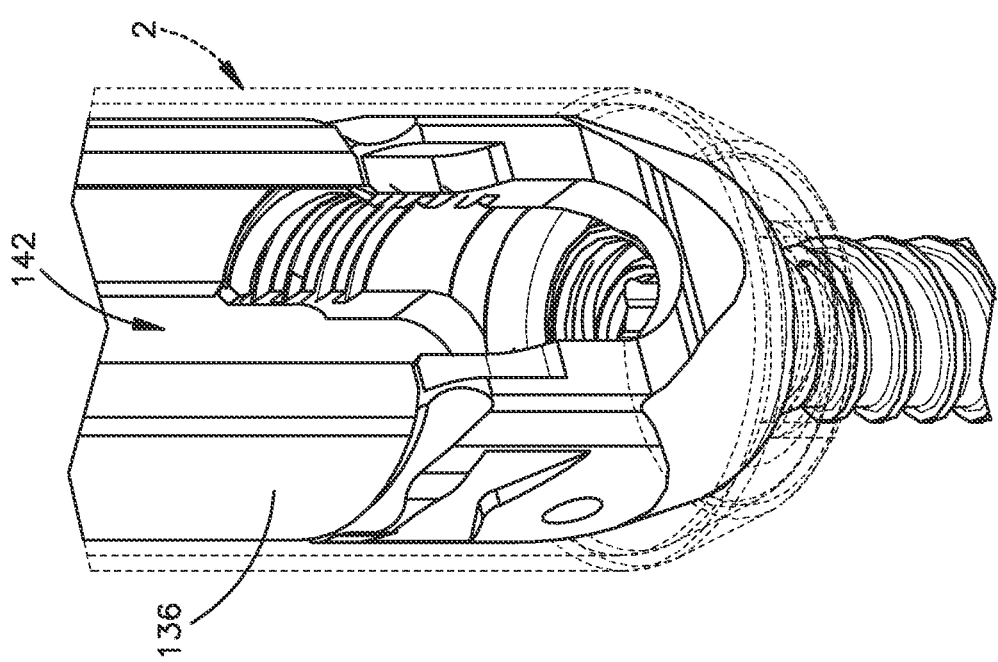

FLEXIBLE SLEEVE FOR BONE FIXATION, AND RELATED SYSTEMS AND METHODS

TECHNICAL FIELD

The present invention relates to a flexible sleeve for coupling to a bone anchor, particularly for extending from an implanted bone anchor to provide a guide channel through soft tissue between the bone anchor and an ex vivo location.

BACKGROUND

Traditional spine surgeries were conducted utilizing an open procedure resulting in a relatively large incision, disruption or resection of significant soft tissue and long recovery times for patients. Minimally invasive techniques have become increasingly popular, particularly for spine surgeries, wherein relatively small incisions and surgical pathways are utilized to perform surgical procedures on a patient, generally resulting in a smaller incision or several relatively small incisions, less retraction and resection of soft tissue and shorter recovery times for patients in comparison to open procedures. Minimally invasive procedures are, in certain circumstances, able to obtain comparable or improved long term surgical outcomes in comparison to open procedures and can provide short term benefits including reduced post-operative pain, reduced use of post-operative narcotics, reduced tissue disruption, thereby permitting reduced scar tissue and potential benefits if a revision is necessary, reduced blood loss, accelerated recovery time, shorter hospital stays and cosmetically appealing smaller incisions. However, the smaller incision or incisions diminish the line-of-sight for a surgeon to directly view a surgical site, because patient soft tissue often limits a surgeon's ability to view the surgical site.

A common procedure in spine surgeries involves fixing screws to several vertebra and securing the screws and vertebra relative to each other with a rod. Such spinal constructs are typically implanted by mounting enclosed or substantially enclosed rigid cannulae or sleeves to the screws such that the enclosed rigid cannulae or sleeves create a surgical pathway through soft tissue and provide access for the surgeon to the surgical site. Minimally invasive spine instruments utilized for such procedures, such as those employing K-wires, can be difficult to assemble, tend to be bulky and extend a significant distance out of a patient's skin, limit a surgeons ability to view the surgical site, and can also inhibit imaging utilizing a C-arm or Fluoroscope as a result of their size and material composition and may be difficult to detach from the screws at the conclusion of the procedure. In addition, current minimally invasive fixation of screws and placement of rods in spine surgery often result in undesirable levels of trauma to a patient's soft tissue in and around the surgical site, along the surgical pathway and proximate the incision. Once assembled for rod insertion, these conventional minimally invasive systems are typically locked into a predetermined position and inhibit a surgeon's options in adapting their surgical technique to a particular patient's anatomy or in adapting the instruments to implant the components in a manner that would benefit the patient.

SUMMARY

According to an embodiment of the present disclosure, a flexible tubular member for guiding insertion of instrumentation to a bone screw affixed within bone includes a tubular body that is flexible, constructed of textile material, and defines a longitudinal axis. The tubular body also defines a proximal end and a distal end opposite each other along the longitudinal axis. The tubular body further defines a guide channel that extends from a proximal opening at the proximal end to a distal opening at the distal end. An attachment member is located at the distal end of the tubular body and is configured to couple the distal end to a proximal portion of the bone screw. The attachment member has an annular shape around the guide channel and is configured to expand responsive to a predetermined tensile force applied to the tubular body for decoupling from the bone screw.

According to another embodiment of the present disclosure, a system for bone fixation includes a bone screw having a head and a shaft extending therefrom toward a distal end of the bone screw in a distal direction. The head also defines a tapered portion that narrows in the distal direction. The system includes a sleeve that is flexible and constructed of textile material. The sleeve defines a longitudinal axis and a proximal end and a distal end opposite each other along the longitudinal axis. The sleeve also defines a guide channel that extends from a proximal opening at the proximal end to a distal opening at the distal end. An attachment ring is located at the distal end of the sleeve and is configured to couple the distal end of the sleeve to the tapered portion of the bone screw. The attachment ring extends annularly around the guide channel and is configured to expand responsive to a predetermined tensile force applied to the sleeve for decoupling the sleeve from the bone screw.

According to an additional embodiment of the present disclosure, a method for securing a bone screw to bone includes attaching a flexible sleeve to a head of the bone screw such that the sleeve extends proximally from the bone screw. Attaching the sleeve involves advancing the bone screw through a guide channel defined by the sleeve until a distal surface of the head contacts an attachment ring located at a distal end of the sleeve. The attachment ring defines an inner diameter that is less than a maximum diameter of the head. The method includes inserting a driver into a socket defined by the head, advancing the bone screw through soft tissue to a fixation site of the bone; and rotating the driver about a central axis, thereby driving a shaft of the bone screw into the fixation site such that the sleeve extends through the soft tissue and a proximal end of the sleeve is located ex vivo. The method also includes applying a tensile force to the sleeve, thereby forcing expansion of the attachment ring for decoupling the sleeve from the bone screw.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 8 is a plan elevation view of the sleeve coupled to a bone anchor and a drive tool of the spinal surgery system illustrated in FIG. 7;

FIG. 9 is a plan elevation view of the sleeve guiding insertion of a second drive tool carrying an extension member of the spinal surgery system illustrated in FIG. 7 toward the bone anchor;

FIG. 12 is an enlarged perspective view of a distal portion of the extension member illustrated in FIG. 11 shown residing in the sleeve and coupled to the bone anchor;

FIG. 13 is a perspective view of the distal portion of the flexible sleeve illustrated in FIG. 12 coupled to the bone anchor;

FIG. 14 is a perspective view of the distal portion of the flexible sleeve illustrated in FIG. 13, wherein an attachment member of the sleeve is broken and the sleeve is partially withdrawn, exposing a distal portion of the extension member that is coupled to the bone anchor;

DETAILED DESCRIPTION OF ILLUSTRATIVE EMBODIMENTS

Figure 1:
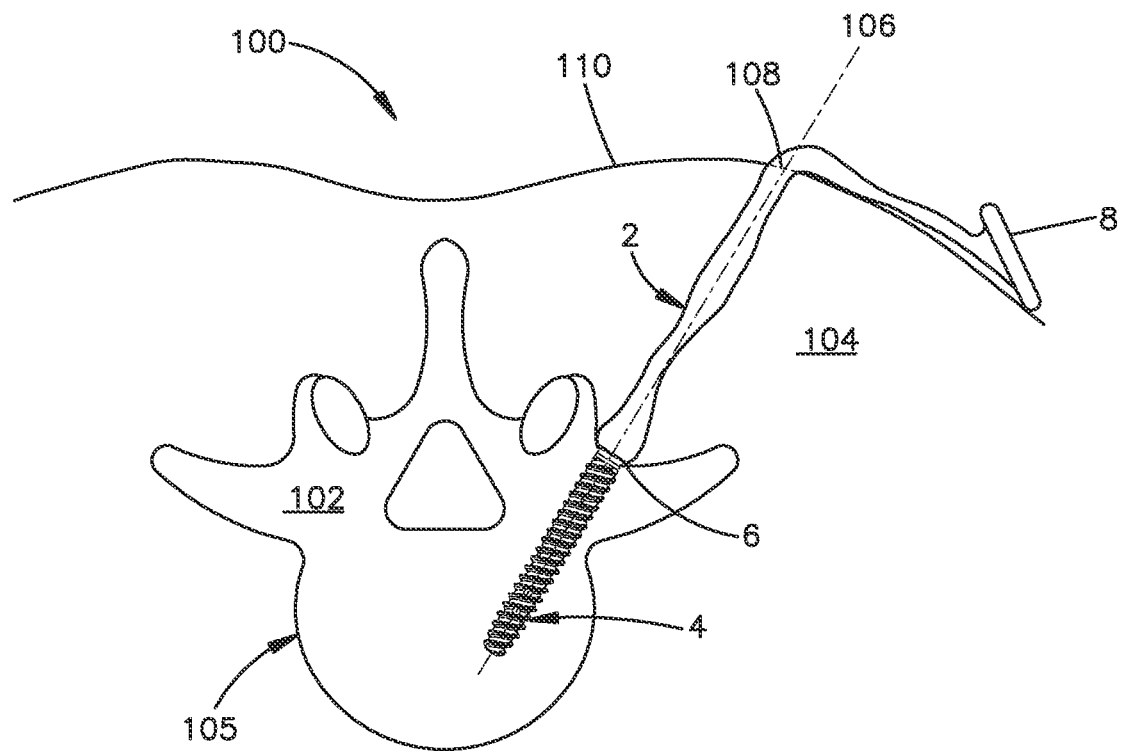
FIG. 1 is a rear plan view of a spinal surgery system that includes a flexible sleeve extending from an implanted bone anchor to an ex vivo location, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

The embodiments described below pertain to flexible sleeves configured to couple to an implant member, such as a bone anchor, and provide a guide channel through soft tissue for guiding insertion of instrumentation and/or additional implant components through the soft tissue to the implant member. For example, current spinal fixation procedures, such as spinal fusion procedures, particularly minimally invasive spinal fusion procedures, tend to employ percutaneous pedicle screws for anchoring to pedicles of one or more vertebral bodies at the surgical treatment site. Such percutaneous pedicle screws commonly comprise a bone screw having a reduced-profile head and a separate extension member that can be coupled to the reduced-profile head of the bone screw. These extension members tend to define a distal anchor head that can be severed or otherwise decoupled form the remainder of the extension member. The anchor head commonly defines a U-shaped channel for receiving a spinal rod therein for affixing a relative position between adjacent vertebral bodies. Alternatively, the anchor head can define a C-shaped channel, such as for use in a screw system configured for side-loading of a spinal rod therein. The anchor head can be configured for polyaxial angulation relative to the bone screw for providing fine adjustability for the orientation of the spinal rod receivable therein.

The current state of the art favors mounting the extension member to the bone screw prior to implanting the bone screw. However, this technique can result in bulky components extending outwardly from the patient, particularly as the number of inserted pedicle screws and attached extension members increases, thereby providing physical obstructions at the surgical site and also obstructing the surgeon's direct line of site. This technique can also impose excessive forces on soft tissue, and can thus result in ischemia therein. Moreover, these components tend to be radiopaque, thus also obstructing electronic imaging of the surgical site, such as radiology and fluoroscopy. However, coupling the extension members to the bone screws in vivo also poses challenges, particularly in that it tends to be difficult to located the heads of the bone screws blindly in the patient, especially if the surgeon is limited to percutaneous access to the implanted bone screw. Furthermore, coupling the extension member to the head of the bone screw in vivo can be complicated by fluids and/or tissues that might become interposed between mating surfaces of the bone screw and the extension member.

The flexible sleeves disclosed herein provide a reliable guide channel through soft tissue, such as for inserting the extension member. In this manner, the bone screw can be implanted prior to coupling with the extension member, which reduces physical obstruction at the surgical site and provides the surgeon with greater ease of movement during the surgery. Additionally, the flexible material of the sleeve allows the ex vivo portion thereof to be laid substantially flat along the outer surface of the patient's skin, thereby also reducing visual obstruction of the surgical site, including electronic visualization, e.g., fluoroscopy. Furthermore, the flexible sleeve material is preferably constructed to allow the sleeve to expand radially (i.e., outwardly) without reducing the overall length of the sleeve, thereby reducing friction imposed on the surrounding soft tissue.

Referring now to FIG. 1, an exemplary embodiment of a bone fixation system 100 includes a flexible tubular body 2, also referred to herein as a flexible sock or sleeve 2, that is configured to couple to a bone anchor 4, such as a bone screw, that is affixable to a target site in bone 102. The sleeve 2 is configured to extend from a distal end 6 thereof attached to the bone anchor 4 and proximally through soft tissue 104 to a proximal end 8 positioned at an ex vivo location with respect to patient anatomy. The sleeve 2 is configured to guide insertion of implant components and/or instrumentation through the soft tissue 104 to the bone anchor 4. In the illustrated example, the bone anchor 4 is a pedicle bone screw configured for insertion into a vertebral body 105 through a pedicle thereof, and the sleeve 2 extends from the pedicle screw 4 proximally through the soft tissue 104 along a trajectory axis 106 to an incision 108 at a skin line 110 of patient anatomy, and further extends from the incision 108 to the proximal end 8. As shown, the sleeve 2 is preferably configured such that a proximal, ex vivo portion thereof can fold away from the trajectory axis 106 and lay along an outer surface of the patent's skin 110.

Figure 2:
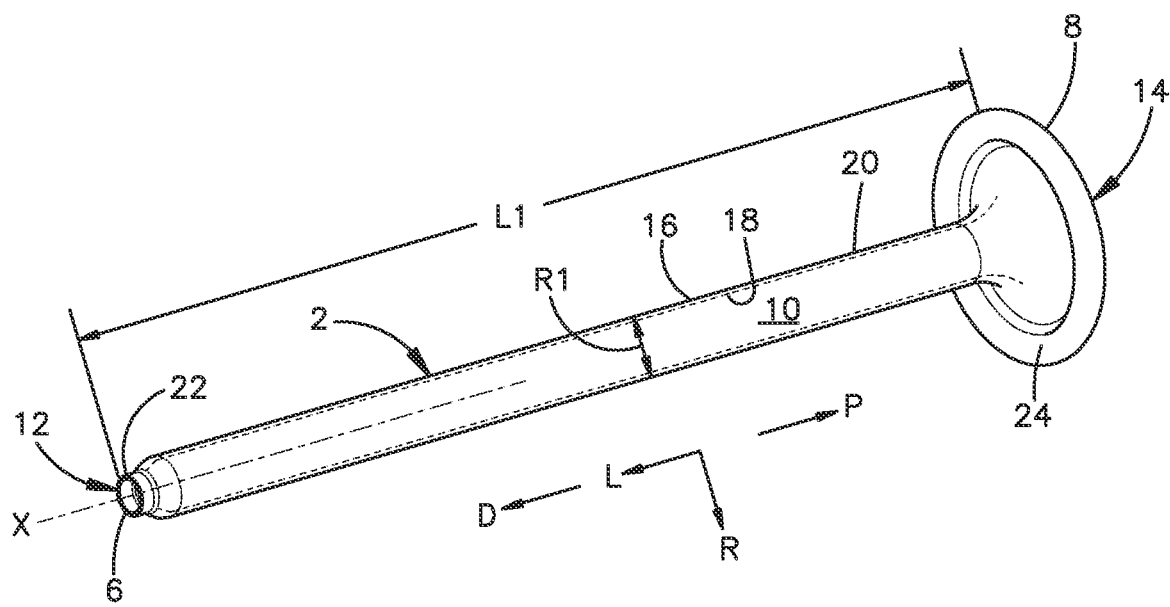
FIG. 2 is a perspective view of the flexible sleeve illustrated in FIG. 1, wherein the sleeve is depicted in a theoretical neutral configuration.

Referring now to FIG. 2, the sleeve 2 is elongate along a longitudinal direction L and defines a longitudinal axis X oriented along the longitudinal direction L. The distal and proximal ends 6, 8 of the sleeve 2 are opposite each other along the longitudinal direction L, such that the distal end 6 is spaced from the proximal end 8 in a distal direction D along the longitudinal direction L, and the proximal end 8 is spaced from the distal end 6 in a proximal direction P along the longitudinal direction L. It should be appreciated that the proximal and distal direction P, D are opposite one other and are each mono-direction components of the longitudinal direction L, which is bi-directional. It should also be appreciated that FIG. 2 depicts the sleeve 2 in a theoretical neutral configuration free of external forces (including gravity).

The sleeve 2 further defines a guide channel 10 that extends along the longitudinal axis X from a distal opening 12 at the distal end 6 to a proximal opening 14 at the proximal end 8. The sleeve 2 also defines an exterior surface 16 and an interior surface 18 spaced from each other along a radial direction R that is perpendicular to the longitudinal axis X (and thus also perpendicular to the longitudinal direction L). A wall 20 of the sleeve 2 extends radially (i.e., along the radial direction R) between the exterior and interior surfaces 16, 18. It should be appreciated that the interior surface 18 defines the guide channel 10.

The sleeve 2 includes an attachment member 22 at or adjacent the distal end 6 for coupling the distal end 6 to a proximal portion of the bone anchor 4, as described in more detail below. The proximal end 8 of the sleeve 2 preferably includes an introduction member 24 configured to facilitate insertion of instrumentation into the guide channel 10. As shown, the introduction member 24 can be a ring that extends annularly around the guide channel 10 and defines the proximal opening 14. The ring 24 is preferably configured to provide a funnel-like structure at the proximal opening 14. The sleeve 2 defines a length L1, measured along the longitudinal direction L from the proximal end 8 to the distal end 6. The sleeve 2 also defines a cross-sectional dimension R1, measured along the radial direction R.

The sleeve 2 is preferably constructed of a textile material, which can be a woven, braided, knitted, and/or electrospun construct. The textile material can be an implant grade biocompatible material, such as polyethylene terephthalate (PET), ultra-high-molecular-weight polyethylene (UHMWPE), polydioxanone (PDS), polypropylene (PP), polyester, and nylon, by way of non-limiting examples. However, it should be appreciated that because the sleeve 2 is configured for temporary use during a surgical procedure and not as a permanent or long-duration implant, the textile material need not be implant grade material, but can be a medical grade material and/or a bio-degradable material.

The sleeve 2 is also preferably configured to be radially compliant, particularly to be capable of expanding radially (i.e., along the radial direction R) and circumferentially while maintaining a substantially constant length. Stated differently, the sleeve 2 is preferably constructed such that the cross-sectional dimension R1 is configured to expand while the length L1 remains substantially constant. Such a configuration can be provided by the manner in which the sleeve 2 is constructed. By way of a non-limiting example, the textile material of the sleeve 2 can be constructed by knitting polyethylene terephthalate (PET) fibers in a weft knit pattern, which provides high radial compliance. Other materials and constructions can be employed to provide the sleeve 2 with high radial compliance. In this manner, the sleeve 2 can expand radially to accommodate passage of implant components and/or instrumentation through the guide channel 10, substantially without lengthening or shortening the length L1, thereby avoiding or at least reducing friction between the exterior surface 16 of the sleeve 2 and the soft tissue 104 adjacent the sleeve 2. The sleeve 2 is also preferably configured to collapse in a substantially flat manner (i.e., without folding in on itself) in the soft tissue 104. In this manner, the sleeve 2 can be configured to avoid compressing the soft tissue 104 that surrounds the sleeve 2. Additionally or alternatively, the sleeve 2 material can also be configured to prevent or at least reduce moisture seepage into the guide channel 10, for example by employing a low porosity. In other embodiments, the sleeve 2 need not inhibit moisture within the guide channel 10. Furthermore, the sleeve 2 is preferably configured to be substantially radiolucent, thereby avoiding obstructing fluoroscopy images. Additionally or alternatively, one or more portions of the sleeve 2 can be partially radiopaque so as to be visible in fluoroscopy or X-ray images. Moreover, the sleeve 2 can be configured to be at least partially visible in magnetic resonance imaging (MRI). This can be achieved, for example, by incorporating metallic filaments in the textile material, by way of a non-limiting example. Additionally or alternatively, the sleeve 2 can carry antibiotic and/or disinfecting liquids to provide therapeutic advantages for soft tissue in contact with or in close proximity to the sleeve 2. Moreover, the textile material of the sleeve 2 can optionally include light emitting fibers, such as for providing illumination within the guide channel 10 and/or for emitting ultraviolet (UV) light for sterilizing soft tissue adjacent the sleeve 2.

Figure 3:
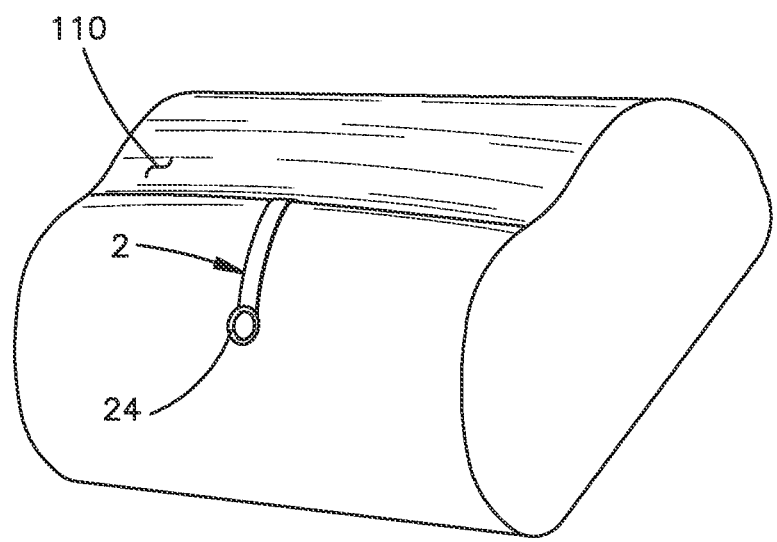
FIG. 3 is a perspective view of an ex vivo portion of the flexible sleeve illustrated in FIG. 1.
Figure 4:
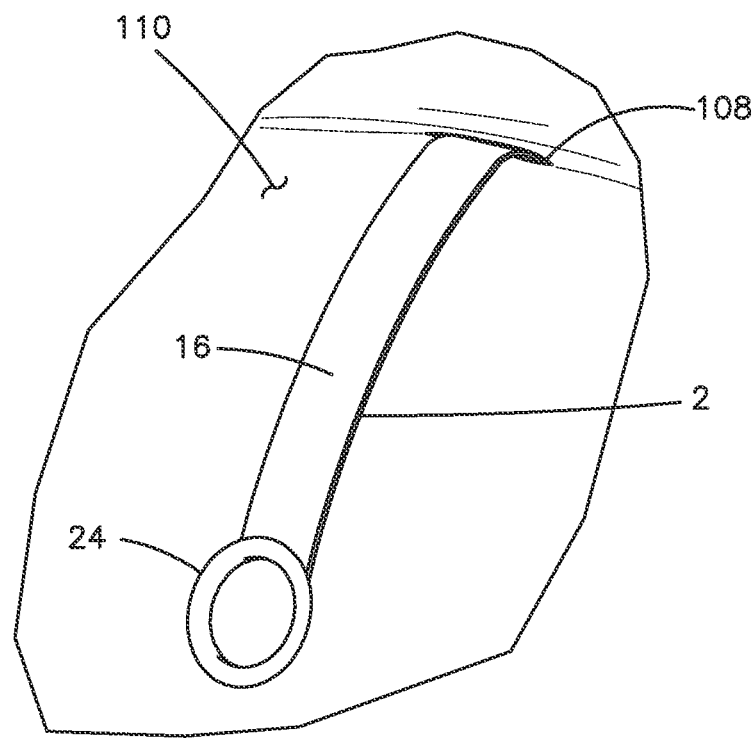
FIG. 4 is an enlarged perspective view of the flexible sleeve illustrated in FIG. 3.

Referring now to FIGS. 3 and 4, the sleeve 2 can also be configured such than any portion thereof, or at least any portion between the attachment member 22 and the introduction member 24, is configured to lay substantially flat when in a resting configuration and when the guide channel 10 thereof is unoccupied. Thus, the physician can lay the ex vivo portion of the sleeve 2 extending from the incision 108 substantially flat along the outer surface of the patient's skin 110. In this manner, the sleeve 2 can advantageously provide access to the implanted bone anchor 4 while reducing obstruction to the surgical site. Stated differently, the ex vivo portion of the sleeve 2 can be folded out of the way until access to the bone anchor 4 is desired. If needed, the physician can manually flatten the ex vivo portion of the sleeve 2, such as by running a finger or thumb along the exterior surface 16 thereof in a manner depressing the sleeve 2 against the skin 110, or by pinching the sleeve 2 between the thumb and forefinger and running the thumb proximally toward the proximal end 8, by way of non-limiting examples.

Figure 5:
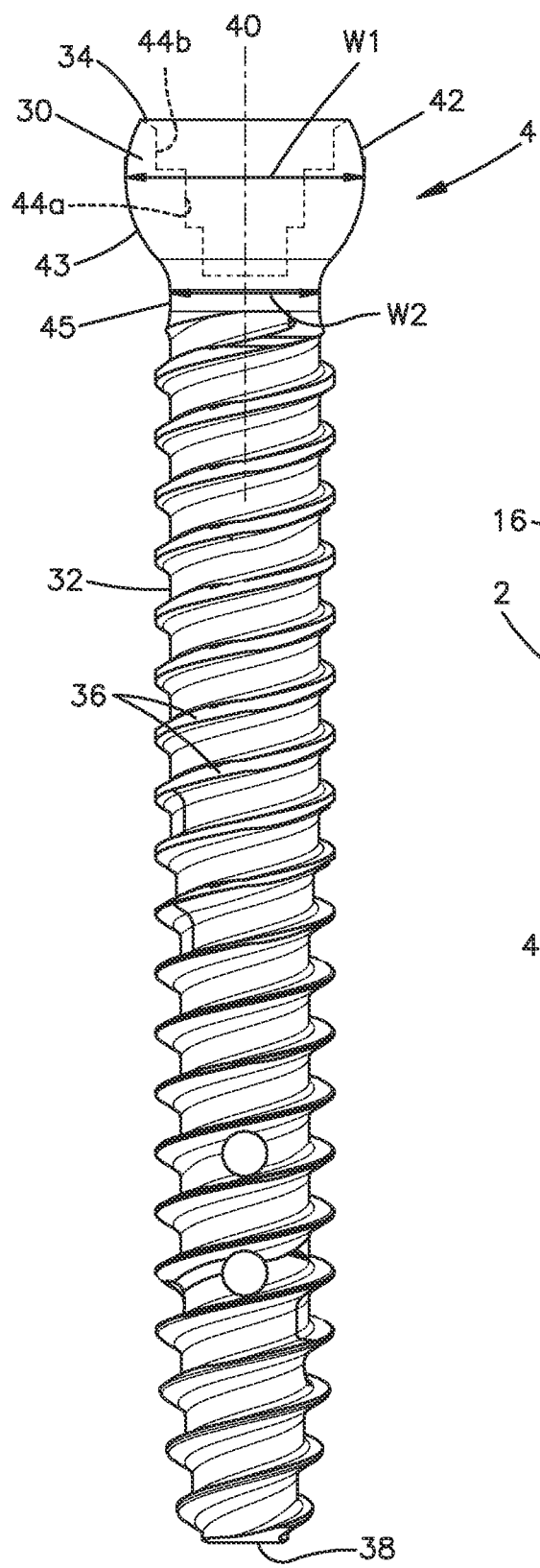
FIG. 5 is a side view of a prior art bone anchor for use with the flexible sleeve illustrated in FIGS. 1-4.

Referring now to FIG. 5, the bone anchor 4 can be a bone screw, such as a pedicle screw, having a head 30 and a shaft 32 extending from the head 30 in the distal direction D. A proximal surface 34 of the head 30 defines a proximal end of the bone screw 4. Accordingly, the proximal surface 34 can be referred to as the proximal end of the bone screw 4. The shaft 32 preferably defines external threads 36 for engaging bone material at the targeting site. The external threads 36 can be helical, as shown, and can extend toward a distal tip 38 that defines a distal end of the bone screw 4. Accordingly, the distal tip 38 can be referred to as the distal end of the bone screw 4. The bone screw 4 defines a central screw axis 40 along the longitudinal direction L. The bone screw 4 preferably defines a cannulation along the central screw axis 40 for receiving receive a guide wire, such as a Kirschner wire or "K-wire", for guiding insertion of the bone screw 4 to the target site.

The head 30 of the bone screw 4 is preferably configured for attachment to an extension member that extends from the bone screw to an ex vivo location. Accordingly, the head 30 depicted throughout the illustrated embodiment does not include external threads, although it should be appreciated that the sleeve 2 can be employed with screw heads that are threaded. The head 30 defines an outer surface 42 that is preferably smooth and has a curvate or semi-spherical shape to facilitate rotation with respect to the extension member, as described in more detail below. Accordingly, the head 30 defines a maximum width W1 and preferably defines a tapered portion 43 that narrows distally (i.e., in the distal direction D) to a neck 45 having a second width W2 that is less than the maximum width W1.

The head 30 also preferably defines one or more sockets 44a,b for receiving one or more complimentary drive tools. As shown, the head 30 can define a first socket 44a configured to receive a first drive tool, such as a driver for driving the bone screw 4 into the target site in the bone 102. The head 30 can also define a second socket 44b configured to receive a second drive tool, such as a driver for driving the extension member into engagement with the head 30, as described in more detail below. Each socket 44a,b can define a drive surface configured to mate with a corresponding bit of the associated drive tool. For example, the drive surface of the first socket 44a can be a star-hex pattern configured to mate with a star-hex drive bit, and the drive surface of the second socket 44b can define internal threading configured to engage external threading on a threaded post drive bit, by way of non-limiting examples. It should be appreciated that other drive surface patterns are within the scope of the present disclosure. The bone screw 4 and the features thereof can be configured as more fully described in U.S. Pat. No. 8,262,662, issued Sep. 11, 2012, in the name of Beardsley et al. (hereinafter the "Beardsley Reference"); U.S. Pat. No. 10,136,923, issued Nov. 27, 2018, in the name of Keyer et al. (hereinafter the "Keyer Reference"); and U.S. Patent Publication No. 2019/0150989, published May 23, 2019, in the name of Biester et al. (hereinafter the "Biester Reference"), the entire disclosure of each of which is incorporated herein by reference.

Figure 6:
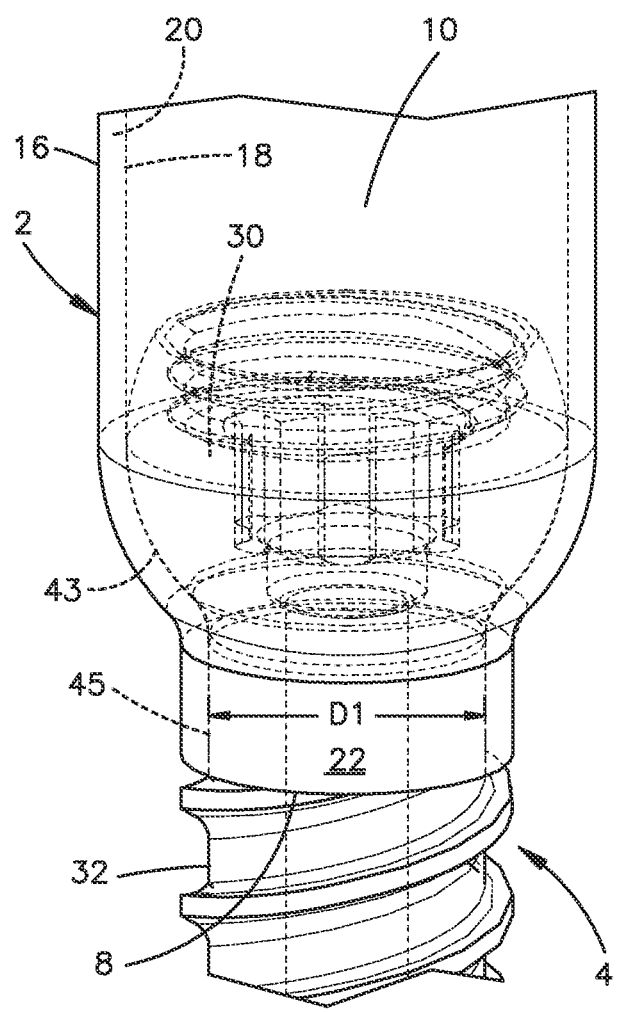
FIG. 6 is a perspective view of a distal portion of the flexible sleeve coupled to a head of the bone anchor illustrated in FIG. 5.

Referring now to FIG. 6, the sleeve 2 is configured to couple to the bone anchor 4, particularly at or adjacent the head 30 thereof. As shown, the attachment member 22 is preferably configured to couple to the bone screw 4 at a location distally spaced from the maximum width W1 of the head 30, such as the neck 45, as shown, or the tapered portion 43 of the head 30, by way of non-limiting examples. The attachment member 22 preferably defines an annular shape that extends around the guide channel 10 at or adjacent the distal end 6 of the sleeve 2. For example, the attachment member 22 can be an annular ring or band, and can define the distal opening 12, although in other embodiment the attachment member 22 can be proximally spaced from the distal opening 12. The attachment member 22 can define an inner diameter D1 that is equivalent to or slightly greater than the second width W2 of the bone anchor 4, such that an inner surface of the attachment member 22 preferably forms a snug fit with an exterior surface of the bone anchor 4, such as at the neck 45 or the tapered portion 43 of the head 30.

The attachment member 22 is also configured to expand, particularly by increasing its inner diameter D1, responsive to a decoupling force, such as a predetermined tensile force applied to the sleeve 2 along the longitudinal axis X. In this manner, the physician can apply the predetermined tensile force to the sleeve 2, such as by pulling on the introduction member 24, when it is desired to decouple the sleeve 2 from the bone anchor 4. By way of a non-limiting example, the attachment member 22 can be defined by a glue, epoxy, or other material configured to be applied in a liquid or semi-liquid phase in a ring annularly around or at least partially around the guide channel 10 and further configured to harden into a solid phase. In other embodiments, the attachment member 22 can be defined by a portion of the sleeve 2 that is at least substantially melted and subsequently solidified into a ring annularly around or at least partially around the guide channel 10. The foregoing example attachment members 22 can be configured to expand by breaking, ripping, tearing, or otherwise undergoing a mode of mechanical failure. In additional embodiments, the attachment member 22 can be a spring member, such an annular or semi-annular spring, such as a slotted or C-shaped ring, or a spiral spring, that is configured to open or otherwise by expand (such as by expanding the inner diameter D1 thereof) responsive to the predetermined tensile force. These embodiments that employ a spring member as the attachment member 22 can be advantageous because they need not undergo a mode of mechanical failure to expand and decouple from the bone screw 4. It should be appreciated that other techniques for constructing the attachment member 22 are within the scope of the present disclosure.

With reference to FIGS. 7-16, further use of the spinal fixation system 100 will be described according to an example surgical procedure. In this example, the surgical procedure is a spinal fusion surgery, such as for providing spinal decompression, although it should be appreciated that the sleeve 2 can be employed with similar benefit for other types of surgical procedures.

Figure 7:
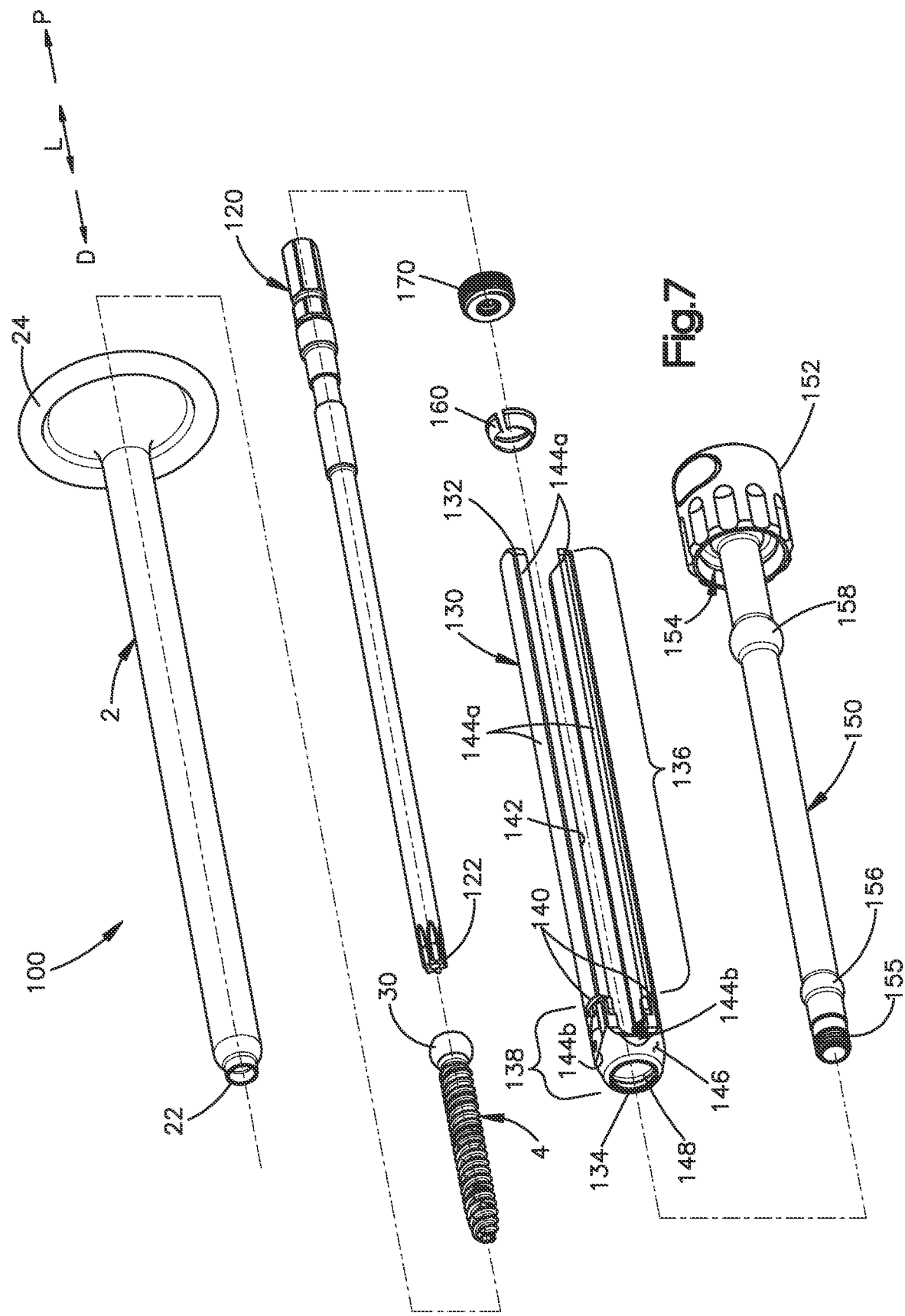
FIG. 7 is an exploded perspective view of a spinal surgery system that employs the flexible sleeve illustrated in FIGS. 1-4.

Referring now to FIG. 7, the spinal fixation system 100 includes the sleeve 2 and the bone anchor 4, as described above, and can further include a first drive member, such as a first drive bit 120 having a distal end 122 configured to engage the first socket 44a of the bone anchor 4 and a proximal end 124 configured to engage a drive tool.

The system 100 can further include an extension member 130 that is elongate along the longitudinal direction L and configured to couple to the head 30 of the bone anchor 4. The extension member 130 defines a proximal end 132 and a distal end 134 spaced from each other along the longitudinal direction L. The extension member 130 can include a main portion 136 that extends distally from the proximal end 132, an anchor head 138 that extends to and defines the distal end 134, and a frangible portion 140 interposed between the main portion 136 and the anchor head 138. The extension member 130 can also define a longitudinally elongate channel 142 that extends along the main portion 136, such as from the proximal end 132, and extends along a portion of the anchor head 138. The elongate channel 142 also extends from opposed sides 144a, 144b of the main portion 136 and the anchor head 138, respectively, along a transverse direction T that is substantially perpendicular to the longitudinal direction L. In this manner, the elongate channel 142 can define a pair of elongate tabs along the main portion 136. Accordingly, the main portion 136 can also be referred to as "extension tabs" 136. The elongate channel 142 is configured for guided insertion of a spinal rod into the anchor head 138, as discussed in more detail below.

The anchor head 138 preferably defines a chamfer surface 146 that extends to the distal end 134 for facilitating advancement of the extension member 130 through the sleeve 2. The anchor head 138 also defines a mounting formation, such as a receptacle 148, configured to receive the head 30 of the bone anchor 4. The frangible portion 140 is configured to break responsive to a predetermined force, such as a predetermined torsion force and/or pulling force, thereby separating the extension tabs 136 from the anchor head 138 after the anchor head 138 couples to the bone anchor 4. The extension member 130, including the extension tabs 136 and the anchor head 138, are more fully described in the Biester and Beardsley References.

The system 100 can include a second drive member, such as a second drive tool 150, configured to extend longitudinally within the elongate channel 142 of the extension member 130 for coupling with the extension member 130 and advancing it through the guide channel 10 of the sleeve 2 to the head 30 of the bone anchor 4. The second drive tool 150 can include a handle 152 located at a proximal end thereof. The handle 152 can define a proximal mounting formation, such as an annular recess 154, for mounting with the proximal end 132 of the extension member 130. The second drive tool 150 can further define a cannulation 153 extending from the proximal to a distal end of the second drive tool 150. The cannulation 153 can be sized to receive the first drive bit 120 therein. In this manner, the second drive tool 150 can advance the extension member 130 through the guide channel 10 of the sleeve 2 and along the first drive bit 120 while the distal end 122 thereof is engaged with the first socket 44a of the bone anchor 4.

A distal end of the second drive tool 150 can define a distal mounting formation, such as a threaded mounting post 155 having external threads for engaging the internal threads of the second socket 44b of the bone anchor 4, thereby locating the head 30 of the bone anchor 4 within the receptacle 148 of the anchor head 138. Such threaded engagement between the threaded mounting post 155 and the internal threads of the second socket 44b effectively holds the bone anchor 4 in place and prevents it from angulating relative to the second drive tool 150 while additional coupling elements are attached to the anchor head 138.

The second drive tool 150 can also include one or more additional formations for carrying one or more associated coupling elements for coupling the anchor head 138 to the head 30 of the bone anchor 4 in secure fashion. For example, the second drive tool 150 can include a first boss 156 for carrying a retention member 160, such as a snap-on collar, for insertion over the head 30 in a manner to reside in the receptacle 148 between the anchor head 138 and the head 30 of the bone anchor 4. The second drive tool 150 can also include a second boss 158 for carrying a locking member 170, such as a locking cap, for engagement with a complimentary locking formation of the anchor head 138 in a manner retaining the spinal rod in the channel 142 of the anchor head 138, as described in more detail below. It should be appreciated that the second driving tool 150 can also include a formation configured to engage a complimentary formation of the main portion 136 of the extension member 130 for applying the predetermined torsion force and/or pulling force thereto and decoupling the main portion 136 from the anchor head 138.

Referring now to FIG. 8, the physician can engage the first drive bit 120 with the bone anchor 4, particularly by inserting the distal end 122 of the bit into the first socket 44a of the head 30 of the bone anchor 4. In the illustrated example, the bone anchor 4 is a pedicle screw 4. The physician can subsequently insert the connected pedicle screw 4 and first drive bit 120 into the guide channel 10 of the sleeve 2 from the proximal opening 14 thereof and advance the pedicle screw 4 and first drive bit 120 distally through the guide channel 10 until the attachment member 22 engages the desired portion of the pedicle screw 4, such as the neck 45 or the tapered portion 43 of the head 30 (shown more clearly in FIG. 6). With the pedicle screw 4, first drive bit 120, and sleeve 2 coupled in this manner, the physician can employ the first drive bit 120 to advance the pedicle screw 4 and a distal portion of the sleeve 2 through an incision, such as a stab incision, through the soft tissue 104 along the trajectory axis 106 to the target site of a first vertebral body 105 and can drive the screw shaft 32 into bone material 102 at the target site. After the shaft 32 is inserted to the desired depth in the first vertebral body 105, the first drive bit 120 can be withdrawn proximally from the guide channel 10, leaving the distal portion of the sleeve 102 within the soft tissue 104 along the trajectory axis 106.

With the first drive bit 120 removed from the sleeve 2, the physician can lay the ex vivo portion of the sleeve 2 flat along the outer surface of the patient's skin and out of the way, as described above. The physician can then use a drive tool, such as the first drive bit 120, to couple a second pedicle screw 4 to a second sleeve 2 and insert the second pedicle screw 4 into a second target site in bone 102, such as into another pedicle, such as a pedicle of a second vertebral body 105 or the opposite pedicle of the first vertebral body 105, with the sleeve extending proximally therefrom through the soft tissue 104 to a second ex vivo location in like manner to the first sleeve 2. The physician can repeat the foregoing steps as needed to insert additional pedicle screws into additional target sites with associated sleeves 2 extending therefrom to respective ex vivo locations. The physician can lay the ex vivo portions of the sleeves 2 flat along the outer surface of the patient's skin to reduce obstruction of the surgical site and also to reduce imaging obstruction.

When it is desired to couple the extension member 130 to the pedicle screw 4, the physician can ensure that the extension member 130 is properly coupled to the second drive tool 150. The physician can manipulate the ex vivo portion of the sleeve 2 into alignment along the trajectory axis 106, such as by lifting the introduction member 24. Referring now to FIG. 9, with the ex vivo portion of the sleeve 2 aligned, the physician can manipulate the second drive tool 150 to insert the distal end 134 of the extension member 130 through the introduction member 24 and into the guide channel 10. The physician can further advance the second drive tool 150 and the extension member 130 coupled thereto distally until the threaded mounting post 155 engages the second socket 44b of the screw head 30.

Figure 10:
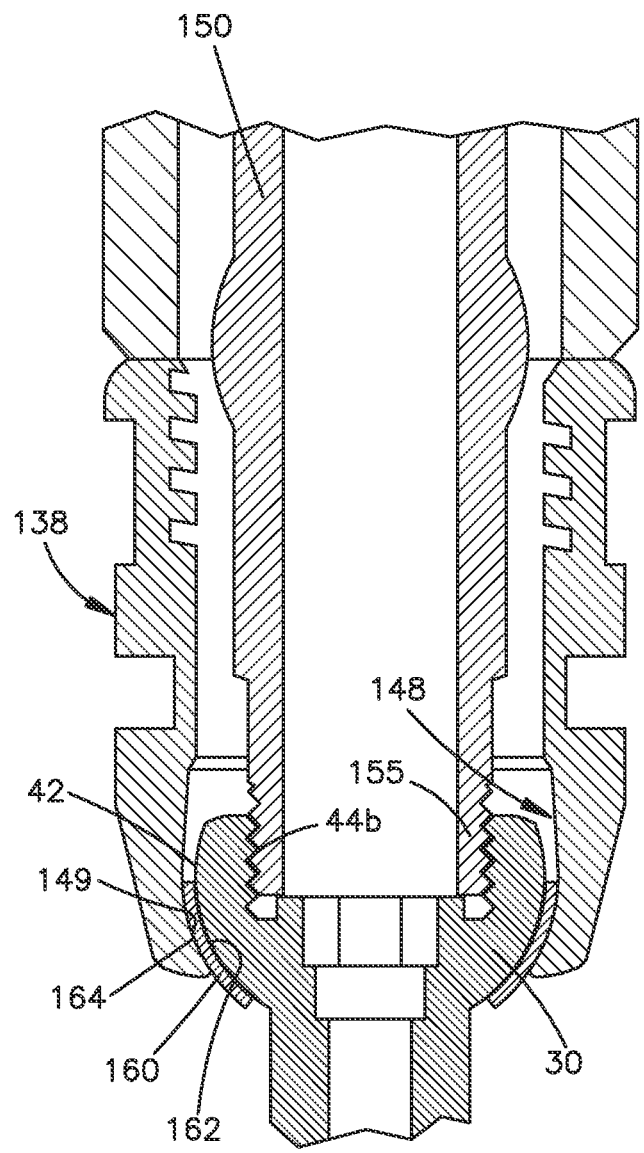
FIG. 10 is a partial sectional side view of the extension member illustrated in FIG. 9 coupled to the bone anchor, wherein the flexible sleeve is omitted for illustration purposes.

Referring now to FIG. 10, the physician can rotate the second drive tool 150 to threadedly mate the threaded mounting post 155 to the internal threads of the second socket 44b until the threaded mounting post 155 is fully seated in the second socket 44b, thereby causing the head 30 to reside in the receptacle 148 of the anchor head 138 at a desired depth. The collar 160 can be advanced distally along the outer surface 42 of the head 30 until the collar 160 is fully seated with respect to the head 30. In its fully seated position, an inner surface 162 of the collar 160 can extend distally across the location of maximum width W1 and along the tapered portion 43 of the head outer surface 42, while an outer surface 164 of the collar 160 engages an interior surface 149 of the anchor head 138 that defines the receptacle 148 thereof. The collar 160 of the illustrated embodiment is configured to snap into place on the head 30 once the distal end of the collar 160 clears the location of maximum width W1, thereby providing the physician with tactile feedback and preferably also auditory feedback (e.g., a snapping or clicking sound) indicating when the collar 160 is fully seated with respect to the screw head 30 and the anchor head 138. The collar 160 is further configured to provide the anchor head 138 with polyaxial angulation with respect to the screw head 30, as described more fully, for example, in the Keyer and Biester References.

Figure 11:
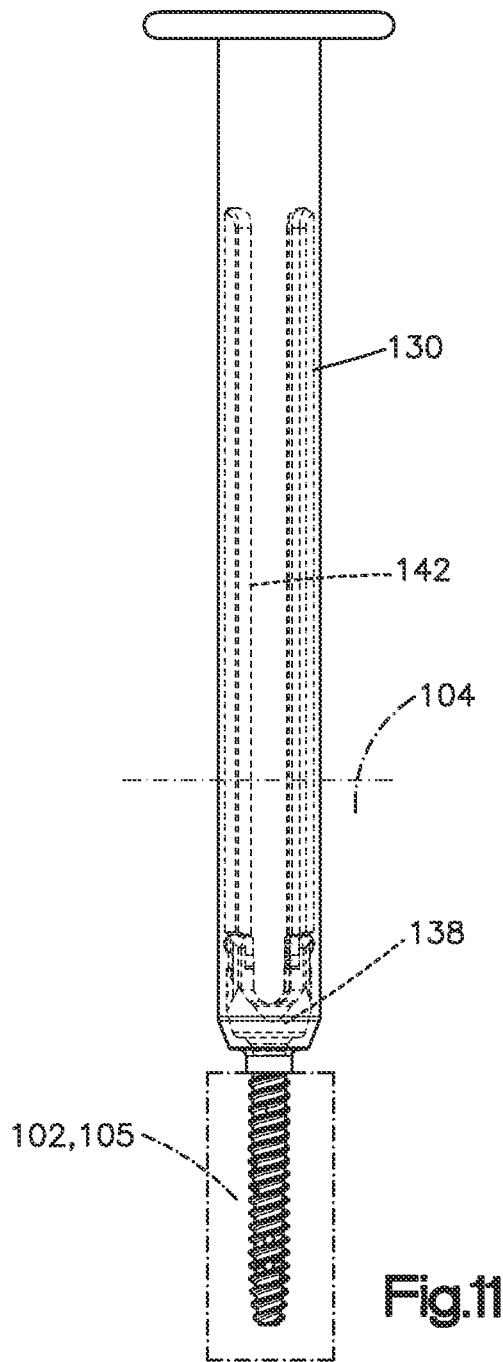
FIG. 11 is a plan elevation view of the extension member illustrated in FIG. 9 coupled to the bone anchor with the second drive member removed from the flexible sleeve.

Referring now to FIGS. 11 and 12, with the anchor head 138 coupled to the pedicle screw 4, the second drive tool 150 can be decoupled from the second socket 44b and withdrawn from the sleeve 2, leaving the extension member 130 within the sleeve 2 and coupled to the pedicle screw 4. The flexibility of sleeve 2 allows the physician to manipulate the extension member 130 through the sleeve 2, such as by gripping around the ex vivo portion of the sleeve 2 that contains the extension member 130, for angulating the extension member 130 polyaxially relative to the pedicle screw 4, as needed, such as to place the elongate channel 146 at a desired orientation for receiving the spinal rod.

Referring now to FIGS. 13 and 14, when it is desired to remove the sleeve 2, the physician can apply the predetermined tensile force F1 thereto, thereby breaking the attachment member 22. The physician can then withdraw the sleeve 2, thereby exposing the extension tabs 136 and the elongate channel 142. In this manner, the sleeve 2 can protect the screw head 30, anchor head 138, and extension tabs 136 in vivo until it is desired to insert the spinal rod in the channel 142.

Figure 15:
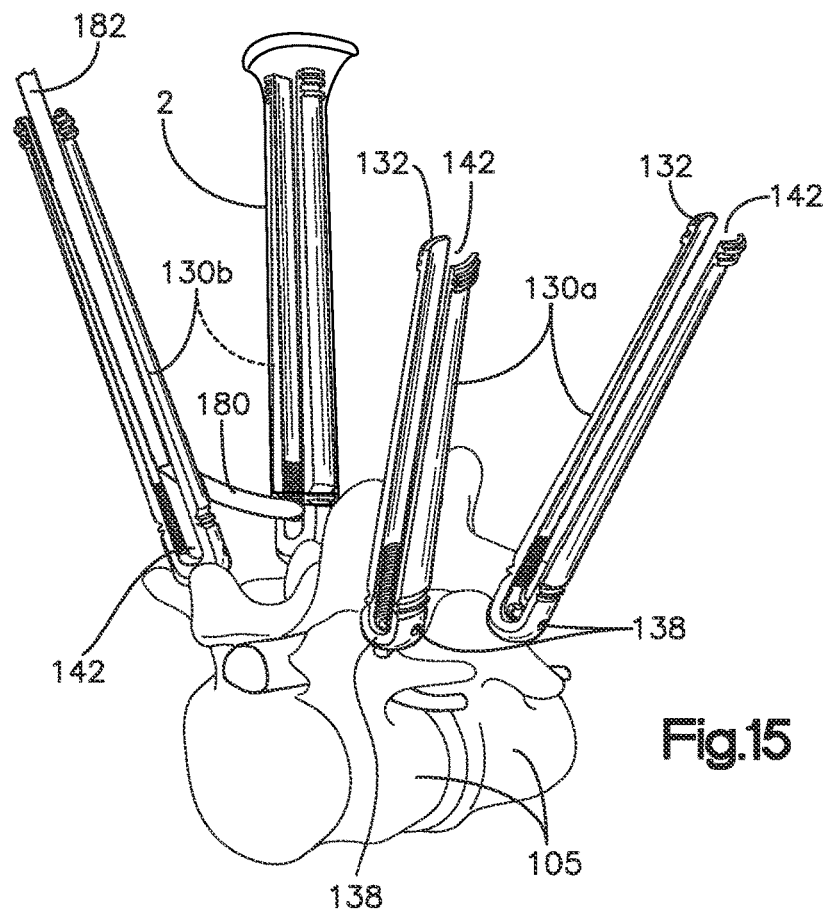
FIG. 15 is a perspective view of various components of the spinal surgery system illustrated in FIG. 7 attached to adjacent vertebral bodies during an intermediate phase of a spinal surgery, according to an embodiment of the present disclosure.
Figure 16:
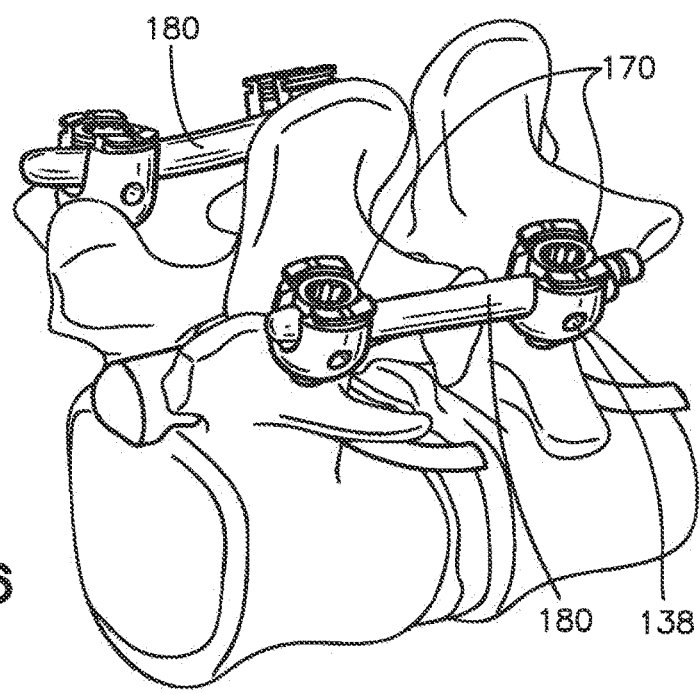
FIG. 16 is a perspective view of various of the components of the spinal surgery system illustrated in FIG. 15 attached to adjacent vertebral bodies during a final phase of the spinal surgery, according to an embodiment of the present disclosure.

Referring now to FIGS. 15 and 16, the physician can repeat one or more of the foregoing steps as needed to insert pedicle screws 4 into a plurality of vertebral bodies, such as a pair of adjacent vertebral bodies 105, and for coupling extension members 130 to the pedicle screws 4. It should be appreciated that the physician can elect to remove a sleeve 2 entirely or only partially from the associated extension tabs 136 for inserting the spinal rod into the elongate channels 142. For example, FIG. 15 shows a first pair of extension members 130a from which the sleeves 2 have been entirely withdrawn. For these extension members 130a, an associated spinal rod 180 can be inserted into the elongate channels 142, such as from the proximal ends 132 of the extension members 130, and the spinal rod 180 can be advanced distally along the channels 142 until the spinal rod 180 is seated in the channels 142 of the anchor heads 138.

Also depicted is a second pair of extension members 130b, one of which has had its associated sleeve 2 fully withdrawn, and the other of which has had its associated sleeve 2 partially withdrawn, exposing a distal portion of the elongate channels 142. For these extension members 130b, the physician can elect to insert the spinal rod 180, such as with assistance of a rod carrying tool 182, distally along the channel 142 of the extension member 130b having had the sleeve 2 fully withdrawn therefrom. The physician can use the tool 182 to insert a distal end of the rod 180 into the exposed anchor head 138 of the extension member 130b having the sleeve 2 only partially withdrawn therefrom. The physician can then seat the rod 180 as desired in both of the associated anchor heads 138. In this manner, at least one of the sleeves 2 can continue to provide a barrier between the soft tissue 104 and the associated extension members 130. Additionally, by distally advancing the spinal rod 180 along only one of the second pair of extension members 130b, less compressive force can be applied to the soft tissue adjacent and particularly between these extension members 130b. The remaining sleeve 2 can optionally remain in place over the associated extension tabs 136 for subsequent operation, thereby reducing entry of in vivo fluids into the associated channel 142, thus providing a cleaner channel 142 for insertion of subsequent members therein, such as the locking cap 170 for locking the spinal rod 180 in the anchor head 128, and also for a decoupling tool that applies the predetermined torsional force and/or pulling force to the frangible portion 140 for decoupling and removing the extension tabs 136. In such embodiments, a portion of the extension tabs 136 can optionally remain within the sleeve 2 while the frangible portion 140 is broken, and the sleeve 2, the extension tabs 136, and the decoupling tool can optionally be removed from the patient in unison. In this manner, the sleeve 2 can be employed to reduce friction and/or abrasion between the extension members 130 and the associated instrumentation during the surgical procedure.

It should be appreciated that the sleeve 2 described herein can be employed with other types of bone fixation procedures or any procedure where it is advantageous to provide a guide channel through soft tissue to a bone anchor.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A system for bone fixation, comprising:
    a bone screw having a head and a shaft extending from the head toward a distal end of the bone screw in a distal direction, wherein the head defines a tapered portion that narrows in the distal direction;

a sleeve that is flexible and constructed of textile material, the sleeve defining a longitudinal axis and a proximal end and a distal end opposite each other along the longitudinal axis, the sleeve defining a guide channel that extends from a proximal opening at the proximal end to a distal opening at the distal end, wherein the sleeve further comprises an introduction member at the proximal end, the introduction member extending annularly around the guide channel and defining the proximal opening;

an attachment ring located at the distal end of the sleeve and configured to couple the distal end of the sleeve to the tapered portion of the bone screw, the attachment ring extending annularly around the guide channel, wherein the attachment ring is configured to expand responsive to a predetermined tensile force applied to the sleeve for decoupling the sleeve from the bone screw; and an extension member elongate along a longitudinal direction, wherein the extension member is configured to advance through the guide channel in the distal direction from the proximal opening and couple to the head of the bone screw, wherein the introduction member defines an inner diameter that is greater than a maximum cross-sectional dimension of the extension member measured along a direction perpendicular to the longitudinal axis.

2. The system of claim 1, wherein the extension member has a main portion, an anchor head that defines a distal end of the extension member, and a frangible portion interposed between the main portion and the anchor head, wherein:

the anchor head defines 1) a chamfer surface that extends to the distal end of the extension member for facilitating advancement of the extension member through the guide channel, and 2) a receptacle configured to receive the head of the bone screw for coupling the anchor head to the head of the bone screw, and the frangible portion is configured to break responsive to a predetermined force, thereby separating the main portion from the anchor head.

3. The system of claim 2, wherein:

the anchor head defines:

an interior surface that defines a bore extending along a central bore axis that extends along the longitudinal direction, wherein the interior surface defines the receptacle; and a transverse channel that extends along a transverse direction substantially perpendicular to the longitudinal direction, the transverse channel configured to receive a spinal rod; and the system further comprises:

a retention member configured to reside within the receptacle, the retention member having an inner surface configured to engage the head of the bone screw and an exterior surface configured to engage the interior surface of the anchor head in a manner maintaining connection between the anchor head and the head of the bone screw; and a locking cap configured to reside in the bore at a proximal end of the anchor head, the locking cap having a locking formation configured to engage a complimentary locking formation defined by the interior surface of the anchor head so as to lock the spinal rod in the transverse channel.

4. The system of claim 3, further comprising:

a first driver configured to engage a socket defined in the head of the bone screw for driving the bone screw into bone; and a second driver configured to advance the extension member through the guide channel and couple the anchor head to the head of the bone screw, the second driver further configured to apply the predetermined force to the extension member for breaking the frangible portion and separating the main portion from the anchor head.

5. A method for securing a bone screw to bone, comprising:

attaching a flexible sleeve to a head of a bone screw such that the sleeve extends proximally from the bone screw, wherein the attaching step comprises advancing the bone screw through a guide channel defined by the sleeve until a distal surface of the head contacts an attachment ring at a distal end of the sleeve, wherein the attachment ring defines an inner diameter that is less than a maximum diameter of the head;

inserting a driver into a socket defined by the head of the bone screw, wherein the driver is disposed in the guide channel of the sleeve while the driver resides in the socket;

advancing the bone screw through soft tissue to a fixation site of the bone;

rotating the driver about a central axis, thereby driving a shaft of the bone screw into the fixation site, wherein the sleeve extends through the soft tissue and a proximal end of the sleeve is located ex vivo;

inserting an extension member from the proximal end of the sleeve ex vivo and advancing the extension member distally through the guide channel until the head of the bone screw resides in a receptacle defined within an anchor head at a distal end of the extension member; and after inserting the extension member, applying a tensile force to the sleeve, thereby expanding the attachment ring for decoupling the sleeve from the bone screw.

6. The method of claim 5, wherein the anchor head is configured to angulate polyaxially relative to the head of the bone screw.

7. The method of claim 5, further comprising:

inserting a spinal rod within a channel defined by the anchor head, wherein the channel extends from opposite sides of the anchor head along a direction substantially perpendicular to the central axis; and advancing a locking member through the guide channel to the anchor head and coupling the locking member to a proximal portion of the anchor head, wherein coupling the locking member affixes the spinal rod to the anchor head.

8. The method of claim 5, further comprising:

breaking a frangible portion of the extension member located longitudinally between the anchor head and a pair of extension tabs, wherein the extension tabs extend to a proximal end of the extension member, and the frangible portion is broken while at least a portion of the extension tabs resides within the guide channel of the sleeve; and removing the extension tabs and the sleeve in unison from the soft tissue.

* * * * *